United States Patent
Sweval et al.

Patent Number: 5,346,669
Date of Patent: Sep. 13, 1994

[54] OZONE-FRIENDLY STERILANT MIXTURE

[75] Inventors: Mark A. Sweval, Lafayette; W. Douglas Register, West Lafayette; Mark L. Robin, West Lafayette; Yuichi Iikubo, West Lafayette, all of Ind.

[73] Assignee: Great Lakes Chemical Corporation, West Lafayette, Ind.

[21] Appl. No.: 162,671

[22] Filed: Dec. 6, 1993

Related U.S. Application Data

[62] Division of Ser. No. 948,094, Sep. 21, 1992.

[51] Int. Cl.$^5$ .................. A01N 29/00; A61L 9/04
[52] U.S. Cl. ........................... 422/34; 422/37; 424/45
[58] Field of Search ............... 422/34, 37; 424/45

[56] References Cited

U.S. PATENT DOCUMENTS

| | | | |
|---|---|---|---|
| 5,039,484 | 8/1991 | Chippett et al. | 422/34 |
| 5,039,485 | 8/1991 | Conviser et al. | 422/34 |
| 5,118,494 | 6/1992 | Schultz et al. | 424/45 |

FOREIGN PATENT DOCUMENTS 0566892 3/1993 European Pat. Off.
1288568 9/1972 United Kingdom ............... 422/34

OTHER PUBLICATIONS

"Sterilization Techniques," Kirk–Othmer Encyclopedia of Chemical Technology, v. 21, pp. 626–644, 1983.

*Primary Examiner*—Robert J. Warden
*Assistant Examiner*—E. Leigh Dawson
*Attorney, Agent, or Firm*—Woodard, Emhardt, Naughton, Moriarty & McNett

[57] ABSTRACT

Non-ozone depleting sterilant compositions made of ethylene oxide and 1,1,1,2,3,3,3-heptafluoropropane. These compositions provide good sterilization characteristics, and are compatible with contemporary environmental concerns. One preferred aspect of the invention is a sterilant mixture comprising from about 20 mole percent to about 35 mole percent ethylene oxide and from about 65 mole percent to about 80 mole percent HFC-227 ea. Compositions comprising from about 25 mole percent to about 30 mole percent ethylene oxide and from about 70 mole percent to about 75 mole percent HFC-227 ea are preferred, with a composition comprising about 27 mole percent ethylene oxide and about 73 mole percent HFC-227 ea being most preferred.

8 Claims, 1 Drawing Sheet

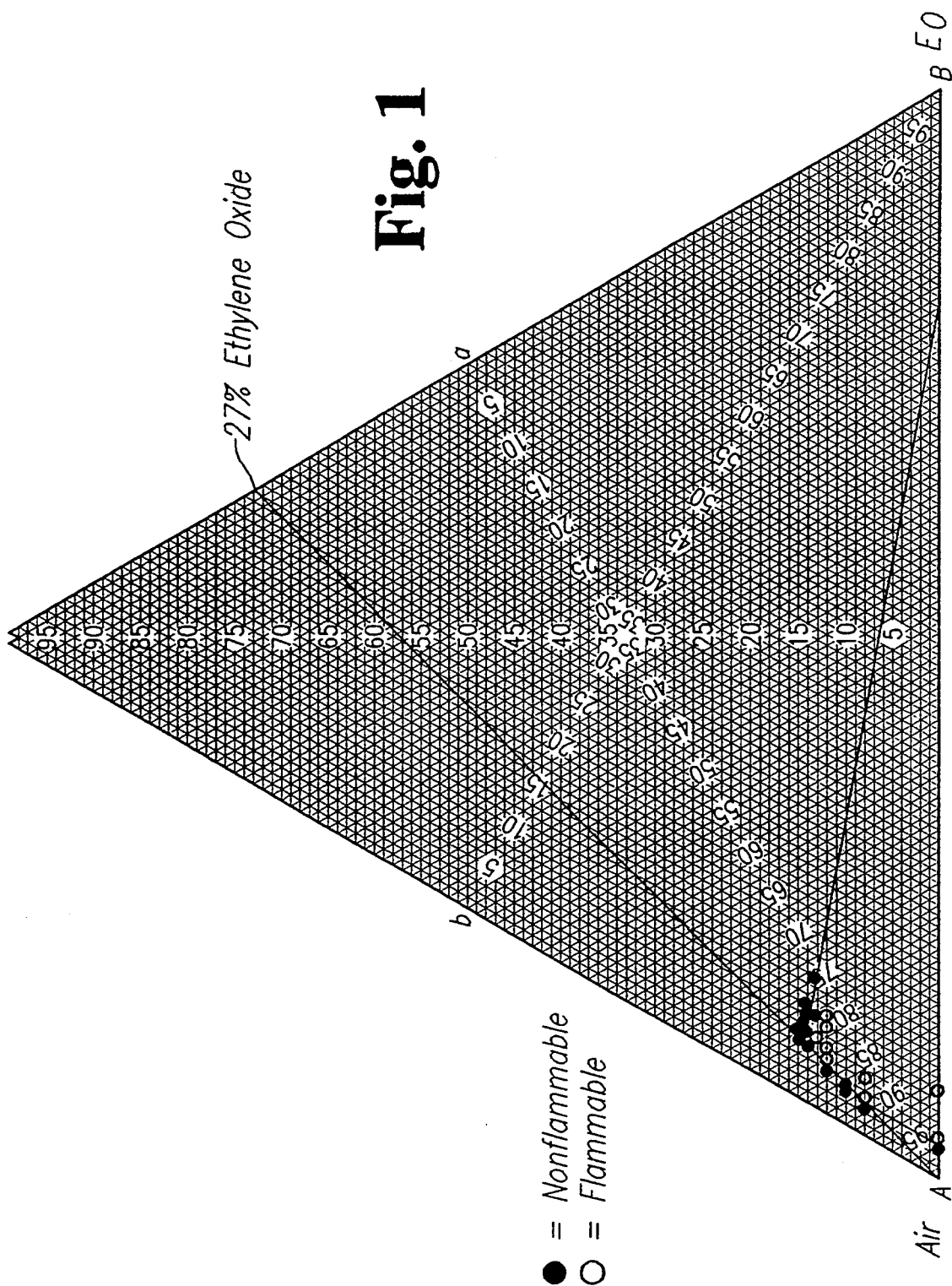

OZONE-FRIENDLY STERILANT MIXTURE

This application is a division of application Ser. No. 07/945,094, filed Sep. 21, 1992.

BACKGROUND OF THE INVENTION

1. Field of the Invention

The present invention relates generally to sterilization mixtures, and more particularly to sterilization mixtures comprised of ethylene oxide and 1,1,1,2,3,3,3-heptafluoropropane.

2. Description Of the Prior Art

Sterilization technology is employed in a wide range of industries and because of this widespread use a variety of sterilization techniques have been developed. One common method of sterilization is dry-heat sterilization, in which the items to be sterilized are heated to a temperature of about 160° C. to 170° C. for several hours. Specific exposures are dictated by the bioburden presented, with higher temperatures requiring less exposure time.

A second common sterilization method is steam sterilization in which a moist heat is applied. Steam sterilization at 100° C. and atmospheric pressure is generally not effective, so elevated temperatures and/or pressures are used. Appropriate temperatures range from about 115° C. to 125° C. or more; pressures range from atmospheric to about 100 psi. The process is most commonly carried out in autoclaves using both elevated pressures and saturated steam.

Although the dry-heat and steam sterilization methods are broadly applicable, certain articles, and particularly those employed in the medical and aerospace industries, cannot withstand the high temperatures of dry-heat sterilization or the moisture of steam sterilization. To sterilize these articles a variety of gaseous sterilants have been developed. These gaseous sterilants typically function at relatively low temperatures and normally comprise anhydrous compositions.

Ethylene oxide is widely employed as the sterilizing agent in sterilization compositions due to its overall effectiveness in that regard. The use of ethylene oxide however is known to have both advantages and disadvantages. One advantage of ethylene oxide is the volatility of its residues. Because ethylene oxide residues volatilize quickly they are less likely to be absorbed by or adsorbed to the articles being sterilized.

One disadvantage of using ethylene oxide in sterilant compositions is its flammability. This flammability requires ethylene oxide to be employed in a carefully controlled manner or to be combined with a fire retardant material. In practice, ethylene oxide is generally not used alone for sterilization. Most often, ethylene oxide is employed in admixture with a fire suppression agent such as carbon dioxide or a fluorocarbon gas.

Over the past several decades, the most commonly employed fire suppression agent for ethylene oxide-based sterilizations mixtures has been the chlorofluorocarbon dichlorodifluoromethane (CFC-12). For example, one commonly employed sterilant mixture comprises 27.3 mole percent (12 weight percent) ethylene oxide and 72.7 mole percent (88 weight percent) CFC-12 and is commonly referred to as 12-88 in the industry. Similar CFC-containing sterilants are also known.

Recent studies have suggested that chlorine-containing compounds such as chlorofluorocarbons and hydrochlorofluorocarbons release chlorine atoms to the stratosphere and may be at least partially responsible for the observed deterioration of the earth's protective ozone layer. Accordingly, the production and use of chlorofluorocarbons, including CFC-12, is being severely restricted and may eventually be banned entirely. Thus, fire suppression agents for ethylene oxide-based sterilizations mixtures that do not contain chlorofluorocarbons are desired for their compatibility with current environmental concerns.

Carbon dioxide has been proposed as one non-CFC-containing diluent for ethylene oxide. Because of its poor inerting characteristics however, a nonflammable mixture of carbon dioxide and ethylene oxide contains less than 40 percent of ethylene oxide per unit volume. As pointed out by Chippett et al. in U.S. Pat. No. 5,039,484, sterilization must therefore be carried out either at higher pressures or for longer contact times.

A further problem associated with the use of carbon dioxide arises from the large difference in boiling points between it and ethylene oxide. This leads to fractionation of the mixture upon withdrawal from the storage tank, and increases the danger of delivering a sterilant mixture rich in either carbon dioxide or ethylene oxide. If the mixture is rich in carbon dioxide it will have poor sterilization characteristics. If it is rich in ethylene oxide it may be explosive.

A need therefore exists for ethylene oxide-based sterilization agents that are safe and effective to use and are environmentally acceptable. The present invention addresses that need.

SUMMARY OF THE INVENTION

Briefly describing one aspect of the present invention, there are provided sterilant compositions comprising ethylene oxide and 1,1,1,2,3,3,3-heptafluoropropane (HFC-227 ea). These compositions provide good sterilization characteristics, and are compatible with contemporary environmental concerns.

One preferred aspect of the invention is a sterilant mixture comprising from about 20 mole percent to about 35 mole percent ethylene oxide and from about 65 mole percent to about 80 mole percent HFC-227 ea.

A further aspect of the invention is a method for sterilizing an article comprising contacting the article with an effective amount of a sterilant mixture including from about 20 mole percent to about 35 mole percent ethylene oxide and from about 65 mole percent to about 80 mole percent HFC-227 ea.

One object of the present invention is to provide ethylene oxide-based sterilization agents that are safe and effective to use and are environmentally acceptable.

Further objects of the present invention will be apparent from the following description and examples.

BRIEF DESCRIPTION OF THE DRAWINGS

FIG. 1 is a flammability diagram for sterilant compositions comprising ethylene oxide and 1,1,1,2,3,3,3-heptafluoropropane.

DESCRIPTION OF THE PREFERRED EMBODIMENT

For the purposes of promoting an understanding of the principles of the invention, reference will now be made to preferred embodiments and specific language will be used to describe the same. It will nevertheless be understood that no limitation of the scope of the invention is thereby intended, such alterations and further modifications in the illustrated embodiments, and such further applications of the principles of the invention as illustrated therein being contemplated as would normally occur to one skilled in the art to which the invention relates.

The invention comprises a sterilant mixture and a method for sterilizing articles employing the sterilant mixture. In particular, sterilant mixtures comprising ethylene oxide and 1,1,1,2,3,3,3-heptafluoropropane (HFC-227 ea) are disclosed. The sterilant mixtures of the present invention preferably comprise from about 20 mole percent ethylene oxide to about 35 mole percent ethylene oxide and from about 65 mole percent HFC-227 ea to about 80 mole percent HFC-227 ea. Compositions comprising from about 25 mole percent to about 30 mole percent ethylene oxide and from about 70 mole percent to about 75 mole percent HFC-227 ea are more preferred, with a composition comprising about 27 mole percent ethylene oxide and about 73 mole percent HFC-227 ea being most preferred. In all compositions the ethylene oxide acts as the active sterilant while the HFC-227 ea acts as a combustion inhibiting agent.

The sterilant mixtures of the present invention may be prepared using any effective mixing technique known to those skilled in the art. Generally, the two components are physically combined as a gaseous composition. The selection of an appropriate process for the production a particular sterilant mixture may be accomplished by one skilled in the art without undue experimentation.

Other components may be present in the sterilant mixture, including inert propellants which may be employed to increase the pressure in the sterilant cylinder and facilitate propelling of the mixture into the sterilization chamber. Suitable propellants include nitrogen, carbon dioxide, argon and trifluoromethane.

The sterilant mixtures of the present invention may be used to sterilize a wide variety of articles, including medical equipment such as syringes, needles, gloves, ampules, dressings, suture, scalpels, catheters, metal or glass containers, etc. The sterilant mixtures may also be used to sterilize rubber and plastic goods, and can be employed as fumigants for materials including furs, bedding, paper goods and other equipment. The sterilant mixtures of the present invention are effective against insects, bacteria, fungi, and various other microorganisms.

In another aspect of the present invention the sterilant mixtures are used to contact specific articles to be sterilized. A sterilizingly effective amount of sterilant mixture is employed in such applications, with specific amounts depending, for example, on the bioburden presented. Preferably, the sterilant mixtures employed in this aspect of the invention comprise from about 20 to 35 mole percent ethylene oxide and from about 65 to 80 mole percent 1,1,1,2,3,3,3-heptafluoropropane. Compositions comprising from about 25 mole percent to about 30 mole percent ethylene oxide and from about 70 mole percent to about 75 mole percent HFC-227 ea are again more preferred, with compositions comprising about 27 mole percent ethylene oxide and about 73 mole percent HFC-227 ea being most preferred.

The pressure at which sterilization takes place can range from about 15 to 50 psia. Sterilization times also will vary, depending on the particular conditions of temperature, humidity, bioburden, sterility assurance desired and material being sterilized. Generally, the contacting is performed for a time sufficient to achieve the desired sterility assurance. Appropriate pressures, temperatures, contact times, etc., may be selected by those skilled in the art without undue experimentation.

The sterilant mixtures of the present invention may be used with any commonly employed sterilizer known to the art, for example those described in detail at 21 Kirk-Othmer Encyclopedia of Chemical Technology 626, in U.S. Pat. No. 5,039,484 to Chippett et al. and in U.S. Pat. No. 5,039,485 to Conviser et al. These sterilizers range from desk-top models to room-size models and even larger.

The following examples serve to further illustrate or distinguish the invention and are not intended to be limiting.

EXAMPLE 1

A series of flammability tests were carried out to determine the flammability curves for ethylene oxide in admixture with HFC-227 ea. Ethylene oxide, HFC-227 ea and air, all at measured concentrations, were mixed in an 8 liter 304 stainless steel vessel at atmospheric pressure and ambient temperature. A 70 Joule DC spark between two electrodes provided ignition energy to the mixture, and flame propagation, i.e., whether or not the mixture ignited and the flame propagated, was determined by temperature and pressure sensors installed at the vessel wall. Flame propagation was deemed to have occurred for any pressure increase of 1.0 psi or greater following activation of the igniter. The data for various mixtures is shown in FIG. 1. A clear data point indicates ignition while a solid point indicates no ignition.

In order for a sterilant mixture to be nonflammable it must be nonflammable at all concentrations of air, i.e., from 0 to 100 percent air. Therefore, a straight line representing 0 to 100 percent air cannot cross below the flammability curve. A straight line from 0 to 100 percent tangent to but not crossing below the flammability curve thus represents the highest ethylene oxide concentration possible while maintaining a nonflammable mixture. Such a line is shown in FIG. 1. It can be seen that mixtures of ethylene oxide and HFC-227 ea can contain up to about 27 mole percent ethylene oxide and still remain nonflammable at all concentrations of air.

EXAMPLE 2

The procedure of Example 1 was repeated with mixtures of ethylene oxide, CFC-12 and air. Again the ingredients were mixed in a stainless steel vessel at atmospheric pressure and ambient temperature. A 70 Joule DC spark between two electrodes provided ignition energy, and flame propagation was again determined by temperature and pressure sensors installed at the vessel wall.

This analysis indicated that mixtures of ethylene oxide and CFC-12 can contain up to approximately 28 mole percent ethylene oxide and yet remain nonflammable at all concentrations of air.

The above examples serve to demonstrate that the sterilant mixtures of the present invention exhibit a nonflammability only slightly less than that of the currently employed mixture of ethylene oxide and CFC-12.

In addition, the mixtures of the present invention do not contribute to the depletion of ozone in the environment. As has been noted above, the disclosed mixtures do not include chlorine and are accordingly not CFC compositions. It is therefore to be appreciated that the sterilant compositions of the present invention have an ozone depletion potential ("ODP") of zero, and that such compositions are believed to be compatible with contemporary environmental concerns.

It is surprising that the sterilant mixture of the present invention provides such beneficial results. As pointed out by Conviser and Woltz in U.S. Pat. No. 5,039,485, the compound HFC-134a, $CF_3CH_2F$, is a poor inertion agent for ethylene oxide. Conviser and Woltz attribute this to the absence of chlorine atoms, and go on to point out that it is well known that the heavier halogens such as chlorine or bromine are the better flame retardants. The inertion efficiency of HFC-227 ea is hence surprising, since this molecule also lacks chlorine.

While the invention has been illustrated and described in detail in the foregoing description, the same is to be considered as illustrative and not restrictive in character, it being understood that only the preferred embodiment has been shown and described and that all changes and modifications that come within the spirit of the invention are desired to be protected.

We claim:

1. A method for sterilizing an article comprising contacting said article with a sterilizingly effective amount of a non-flammable sterilant mixture comprising from about 20 mole percent to about 35 mole percent ethylene oxide, and from about 65 mole percent to about 80 mole percent 1,1,1,2,3,3,3-heptafluoropropane.

2. The method of claim 1 wherein the sterilant mixture has a concentration of from about 25 mole percent to about 30 mole percent ethylene oxide, and a concentration of from about 70 mole percent to about 75 mole percent 1,1,1,2,3,3,3-heptafluoropropane.

3. The method of claim 2 wherein the sterilant mixture has a concentration of about 27 mole percent ethylene oxide, and a concentration of about 73 mole percent 1,1,1,2,3,3,3-heptafluoropropane.

4. The method of claim 1 wherein the ethylene oxide concentration is less than about 28 mole percent and the sterilant mixture is nonflammable in all concentrations of air.

5. The method of claim 1 wherein tile sterilant mixture further comprises an inert propellant selected from the group consisting of nitrogen, carbon dioxide, argon and trifluoromethane.

6. The method of claim 1 wherein said contacting is for a time sufficient to achieve sterilization of said article.

7. The method of claim 1 wherein the sterilant mixture is in gaseous form when it contacts the article.

8. The method of claim 7 wherein said contacting is at a pressure of from about 15 psia to about 50 psia.

* * * * *

UNITED STATES PATENT AND TRADEMARK OFFICE
CERTIFICATE OF CORRECTION

PATENT NO.  : 5,346,669
DATED       : September 13, 1994
INVENTOR(S) : Sweval et al.

It is certified that error appears in the above-identified patent and that said Letters Patent is hereby corrected as shown below:

In column 1, line 5: "07/945,094" should read "07/948,094"

Signed and Sealed this

Twenty-second Day of November, 1994

Attest:

BRUCE LEHMAN

*Attesting Officer*          *Commissioner of Patents and Trademarks*

Disclaimer 5,346,669—Mark A. Sweval, Lafayette; W. Douglas Register, West Lafayette; Mark L. Robin, West Lafayette; Yuichi Iikubo, West Lafayette, all of Ind. OZONE FRIENDLY STERILANT MIXTURE. Patent dated Sept. 13, 1994. Disclaimer filed April 16, 1997, by the assignee, Great Lakes Chemical Corp.

Hereby enters this disclaimer to claims 1-8 of said patent.
*(Official Gazette,* September 9, 1997)